United States Patent [19]

Shaw

[11] 4,206,759

[45] Jun. 10, 1980

[54] SURGICAL INSTRUMENT HAVING SELF-REGULATED VAPOR CONDENSATION HEATING OF ITS CUTTING EDGE AND METHOD OF USING THE SAME

[76] Inventor: Robert F. Shaw, 50 St. Germain, San Francisco, Calif. 94114

[21] Appl. No.: 558,332

[22] Filed: Mar. 14, 1975

Related U.S. Application Data

[63] Continuation-in-part of Ser. No. 534,756, Dec. 2, 1974, Pat. No. 4,089,336, which is a continuation of Ser. No. 63,645, Aug. 13, 1970, abandoned, which is a continuation of Ser. No. 681,737, Nov. 9, 1967, abandoned.

[51] Int. Cl.² ............................................. A61B 17/36
[52] U.S. Cl. .................................... 128/303.1; 30/140
[58] Field of Search .......... 30/140; 128/303.1, 303.13, 128/303.14

[56] References Cited

U.S. PATENT DOCUMENTS

| | | | |
|---|---|---|---|
| 883,343 | 3/1908 | Porter | 30/140 |
| 2,623,977 | 12/1952 | Weiskopf | 30/140 |
| 3,024,342 | 3/1962 | Birnbach et al. | 30/140 |
| 3,117,578 | 1/1964 | Helbling | 128/303.14 |
| 3,502,081 | 3/1970 | Amoils | 128/303.1 |

FOREIGN PATENT DOCUMENTS 550456  10/1956  Italy ......................................... 30/140

*Primary Examiner*—William E. Kamm
*Assistant Examiner*—Michael H. Thaler
*Attorney, Agent, or Firm*—Lyon & Lyon

[57] ABSTRACT

The temperature of the cutting edge of a surgical cutting instrument is maintained within a preselected temperature range for surgical cutting and simultaneous hemostasis by conducting heat from a thermal distributing means that is disposed along the cutting edge of the instrument. The thermal distributing means selectively heats regions of the cutting edge that are locally cooled by the tissue contact of surgical cutting by condensation in the regions of the cooled edge of previously evaporated fluids, with concomitant release of the heat previously absorbed upon evaporation of the fluid.

17 Claims, 4 Drawing Figures

SURGICAL INSTRUMENT HAVING SELF-REGULATED VAPOR CONDENSATION HEATING OF ITS CUTTING EDGE AND METHOD OF USING THE SAME

RELATED APPLICATIONS

This application is a continuation-in-part of U.S. patent application Ser. No. 534,756 filed Dec. 2, 1974 now U.S. Pat. No. 4,089,336, which is a continuation of U.S. patent application Ser. No. 63,645 filed Aug. 13, 1970, now abandoned, which is a continuation of U.S. patent application Ser. No. 681,737 filed Nov. 9, 1967, now abandoned.

BACKGROUND OF THE INVENTION

The control of bleeding during surgery accounts for a major portion of the total time involved in an operation. The bleeding that occurs from the plethora of small blood vessels that prevade all tissues whenever tissues are incised obscures the surgeon's vision, reduces his precision, and often dictates slot and elaborate procedures in surgical operations. It is well known to heat the tissues to minimize bleeding from incisions, and surgical scalpels which are designated to elevate tissue temperatures and minimize bleeding are also well known. One such scalpel transmits high frequency, high energy sparks from a small electrode held in the surgeon's hand to the tissues, where they are converted to heat. Typically, substantial electrical currents pass through the patient's body to a large electrode beneath the patient, which completes the electrical circuit. Discharge of sparks and temperature conversion in the tissue are poorly controlled in distribution and intensity, and erratic muscular contractions in the patient are produced so that this apparatus cannot be used to perform precise surgery. Further, apparatus of this type frequently produce severe tissue damage and debris in the form of charred and dead tissue, which materially interfere with wound healing.

Another well-known surgical scalpel employs a blade with a resistive heating element which cuts the tissue and provides simultaneous hemostasis. Although these resistive elements can be readily brought to a suitably high and constant temperature in air prior to contacting tissues, as soon as portions of the blade in contact with tissues, they are rapidly cooled. During surgery, non-predictable and continuously varying portions of the blade contact the tissues as they are being cut. As the blade cools, the tissue cutting and hemostasis become markedly less effective and tissue tends to adhere to the blade. If additional power is applied by conventional means to counteract this cooling, this additional power is selectively delivered to the uncooled portions of the blade, frequently resulting in excessive temperatures which may result in tissue damage and blade destruction. This results from the fact that in certain known resistively heated scalpels, the heating is a function of the current squared times the resistance ($I^2R$). In conventional metallic blades of this type, the higher the temperature of any blade portion, the greater its electrical resistance, and consequently the greater the incremental heating resulting from incremental power input.

It is generally recognized that to seal tissues and effect hemostasis it is desirable to operate at a temperature between 300° C. and 1000° C. And for reasons noted above, it is desirable that electrothermal hemostatic surgical cutting instruments include a mechanism by which power is selectively delivered to those portions of the blade that are cooled by tissue contact so that the cutting edge may be maintained at a substantially uniform operating temperature within the desired optimal range. Recently, hemostatic scalpels have been described (see, for example, U.S. Pat. Nos. 3,768,482 and 3,826,263) in which the temperature-controlling mechanisms include resistive heating elements disposed on the surface of the scalpel blade. However, such instruments require precision in fabricating the dimensions of the heating elements to obtain the desired resistances. And such resistive heating elements may be subjected to variations in resistance during use, as tissue juices and proteins become deposited upon the surface of the blade.

SUMMARY OF THE INVENTION

The present invention provides a surgical cutting instrument in which the temperature of the cutting portion of the blade is elevated and maintained within a preselected and relatively constant temperature range along its length by conducting heat to the cutting edge from a thermal distribution means in which heat absorbed by evaporation of a fluid is subsequently released by condensation of that fluid to selectively heat those portions of the cutting edge that are cooled upon contact with tissue being cut. The thermal distribution means consists of a closed evacuated chamber containing both a fluid and a capillary action liquid transport means for returning the condensed liquid to the heat source, and is disposed in the region of the blade along its cutting edge.

A heat source is coupled to the thermal distribution means to elevate the temperature of the fluid contained therein above its solidification temperature, which temperature is within or slightly above the preselected operating temperature range of the cutting edge. Heating of the cutting edge is provided by thermal conduction from the chamber wall. Selective heating of regions of the cutting edge that are locally cooled upon contact with tissues being cut is provided for by condensing the previously-vaporized fluid on the contiguous cooled portions of the chamber wall to release a portion of the thermal energy which was previously stored in the vapor and which was required to convert the fluid from its liquid phase to its vapor phase. The condensed liquid is transported by capillary action of a wick-like structure disposed along the wall of the chamber to the region of the heat source where it is once again vaporized. This removes the liquid from the capillary action transport means and stores thermal energy therein. The vapor phase of the liquid is transported to cooled regions of the chamber by local pressure differentials within the chamber which result from (1) the pressure increments associated with vaporization, and (2) from the pressure decrements associated with condensation. The vaporized fluid thus stores thermal energy at substantially the temperature at which the vapor is created and releases stored thermal energy upon contact with colder surfaces. Whenever and wherever the vapor encounters a colder surface, the vapor condenses and releases the heat previously required to vaporize the liquid. The processes of vaporization and condensation are essentially independent and are interrelated only by streams of vapor and liquid in the chamber. The result is that the temperature along the entire length of the chamber tends to remain constant, and the temperature of the cutting edge of the blade which is thermally coupled to the chamber along its length thus also tends to remain constant.

Thermal conduction from the thermal distribution means to the cutting edge occurs substantially from only the relatively small portion of the chamber wall contiguous to the cutting edge. An electric heating element is disposed along the length of the chamber wall about a circumferential portion thereof which is opposite the cutting edge. This longitudinal disposition of the electric heating element along those portions of the chamber which are opposite to the portions of the chamber that are contiguous to the cutting edge permits more efficient operation of the thermal distribution means for three reasons. First, the large surface areas of the chamber wall that are contiguous to the electric heater do not require condensation of previously evaporated working fluid with concomitant release of heat to bring these portions of the thermal distribution means to the elevated operating temperatures required for hemostasis. Second, the longitudinal arrangement of the electric heating element allows the vapor to be transported from the regions of the chamber contiguous to the electric heater to nearby regions of the chamber that are contiguous to the cutting edge substantially along lateral (i.e., diametric paths, rather than primarily along longitudinal paths running through the length of the chamber. Third, the longitudinal disposition of the electric heating element upon the chamber wall results in much of the capillary transport of condensed liquid occurring along circumferential rather than longitudinal paths. These shorter vapor and liquid paths result in shorter, quicker and more efficient cycling of the working fluid.

Because the longitudinal disposition of the electric heater means results in shorter vapor transport paths, the vapor conducting channel of the thermal distribution means can be reduced to a size sufficiently small to be practical for a surgical instrument where good visibility of the cutting edge is required.

Materials suitable for operating as the working fluid in the thermal distribution means within a temperature range which is satisfactory for hemostatic surgery include sodium, potassium, lithium, cesium, mercury and other materials. The capillary action for transporting the liquid along the chamber wall from areas of condensation to areas of vaporization may be supported by such liquid transport means as screen mesh structures, sintered fibers, porous surfaces adjacent to the interior surface of the chamber, or by fine grooving of the chamber wall. The liquid transport means also provides for separation of liquid and vapor flow, thereby minimizing the entrainment of condensed liquid within countercurrent flow of vapor.

DESCRIPTION OF THE PREFERRED EMBODIMENT

Figure 1:
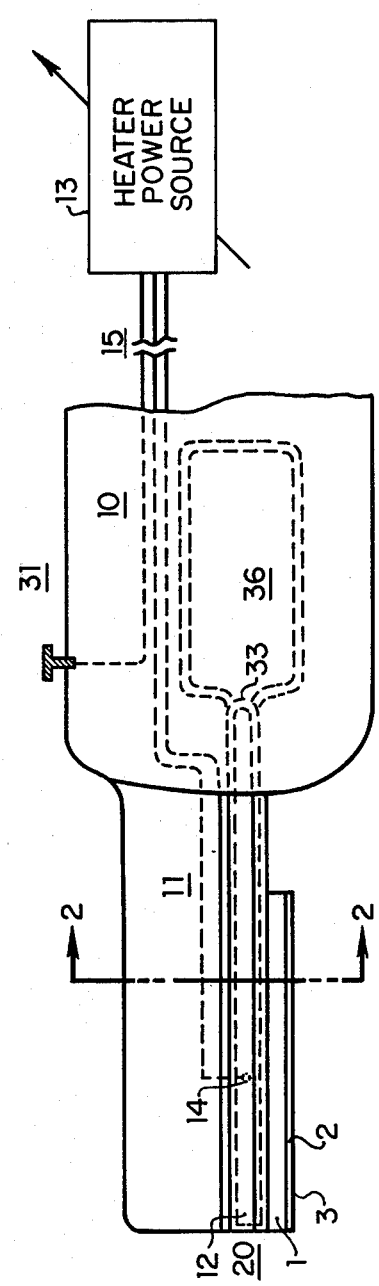
FIG. 1 is a side view of one embodiment of the hemostatic scalpel according to the present invention.
Figure 2:
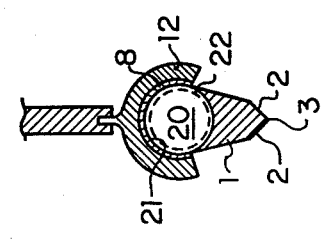
FIG. 2 is an end sectional view of the scalpel of FIG. 1.

Referring now to FIGS. 1 and 2, there is illustrated one embodiment of the present invention in which blade portion 1 that is made of a thermally-conducting material may be attached to the extension 11 of handle portion 10 to form the surgical instrument. Facets 2 are formed along the length of the lower border of blade 1 to establish the cutting edge 3 of the instrument. The extension 11 of handle portion 10 includes the thermal distribution means 20, the heater means 8, and the thermal insulating means 12. The heater means 8 is disposed contiguous to and in good thermal contact with the upper circumference of chamber wall 21 of the thermal distribution means 20 throughout its length, and thermal insulating means 12 is disposed over the heater means 8. The lowermost circumference of chamber wall 21 is in close mechanical and thermal contact with the cutting portion of blade 1.

Chamber wall 21 forms a fluid-tight container of the thermal distribution means 20 which includes liquid transport means 22 disposed in both circumferential and longitudinal contiguity to chamber wall 21. The liquid transport means 22 includes a fine mesh screen, fine grooves or other capillary means which may be of the order of 10 mils wide and 10 mils deep on the inner surface of chamber wall 21 to provide a conduit for the travel of the liquid by capillary action. Other suitable wicks or capillary-action structures may be disposed in both a circumferential and longitudinal direction.

Prior to forming chamber walls 21 into a fluid-tight compartment, a quantity of working fluid is introduced into the thermal distribution means 20 sufficient to saturate the wick-like liquid transport means 22 with the liquid at a selected temperature and pressure. This working fluid may be sodium, potassium, lithium, mercury or cesium. These metals are suitable for operation in the desired temperature range because of their excellent thermal conductivity and their high surface tensions which facilitate their transport by capillary action. Of these, potassium and mercury may be preferred because they offer the highest heat transport capacity at lower operating temperatures.

Heater means 8 in the embodiment shown in an electrical resistance heater consisting of electrically insulated high resistance conductors disposed in a suitable pattern in direct thermal contact with the outside surface of the upper circumference of chamber wall 21, or the inside surface of a high-conductivity, high-emissivity material, which in turn is in good mechanical and thermal contact with chamber wall 21. Heater means 8 is energized by the heater power source 13 which is activated by closure of switch 31 in handle 10, under the control of the operating surgeon. A temperature sensor 14 disposed upon and in good thermal contact with chamber wall 21 monitors the temperature of the external surface of the thermal distribution means, preferably in its lower circumference, and produces a representative control signal on line 15 for selectively altering the output of power source 13 in a conventional manner when activated by switch 31 as the temperature of the thermal distribution means 20 approaches a preselected temperature. Alternatively, a pressure sensor means 14 can be disposed to monitor the pressure within the chamber 21 of the thermal distribution means 20 to alter the power supplied to the heater means 8 from source 13 in a manner similar to the one described above with reference to a temperature transducer.

Upon activation of switch 31, the source 13 supplies power to the heater means 8 which thus heats the upper regions of the chamber walls 21. This heating of the chamber wall 21 vaporizes some portion of the working fluid within the chamber of the thermal distribution means 20. The heated vapor rapidly distributes heat over the entire inner surface of the chamber which, in turn, heats the cutting edge portion 1 of the blade. As the temperature of the chamber and, hence, of the cutting edge approaches the desired operating temperature, as monitored by sensor 14, the power source 13 delivers progressively less power merely to maintain the cutting edge at the preselected temperature with the scalpel in the air, an operating condition for which the heat losses are minimal.

As the blade 1 is manipulated to incise tissues, heat losses will increase substantially from the portions of the blade which contact the tissue being cut, thus cooling such portions of the blade and the portions of the chamber wall 21 in thermal contact therewith. Vapor in this region of the chamber of the thermal distribution means 20 will condense upon the cooled region of chamber wall 21, thereby liberating the latent heat of vaporization and selectively heating such cooled portions of the chamber wall 21 that are thermally coupled to the overlying cooled regions of the blade 1. The pressure will decrease in the regions of the chamber where the walls 21 are cooled. Vapor from other regions of the chamber adjacent the heater means 8 will move axially and laterally along the vapor channel that is formed within the central region of the chamber 21 in response to the pressure gradients that are established toward the area of condensation. Heating of locally-cooled regions of the chamber walls (and of the blade 1) by condensation of vapor will continue in this manner as long as cooling by heat loss in such regions continues. The working fluid which is thus condensed in locally-cooled regions is transported to regions of the chamber that are adjacent the heater means 8 by capillary action of the mesh screen 22 (or other capillary structure) where it is again vaporized. Decreases in the average temperature or pressure within the chamber of the thermal distribution means 20, as sensed by either a thermal or pressure sensor 14, controls the power source 13 to increase the power supplied to the heater means 8. Increased heating thus accelerates the rate of vaporization of the working fluid. Thus, vaporized fluid travels along the vapor channel to cooler regions of the chamber 21 where it is condensed and transported by capillary action from the region of condensation back to the regions of vaporization in a continuous manner.

The thermal cycle may be considered as follows:

Vaporization of the working fluid stores thermal energy in the vapor which is then transported by pressure gradients to cooler regions where the vapor condenses and gives up substantially the stored thermal energy. The condensed liquid is then transported by capillary action back to regions that are depleted of liquid due to heating and vaporization.

It should be noted that because the heater means 8 is disposed along the entire length of the thermal distribution means 20, the distances can be made small between regions of thermal distribution means 20 that are adjacent the heater means 8 (i.e., upper circumference of chamber wall 21) and regions of the thermal distribution means 20 that are adjacent the blade 1 (i.e., lower circumferences of chamber wall 21). Because the regions of the thermal distribution means 20 and the heater means 8 adjacent thereto are thermally insulated, the heat transfer is predominantly restricted to the course from the heater means 8 to the blade 1 via the thermal distribution means 20 operating in the manner previously described. The surface temperature of handle 10 and the extension 11 may therefore be maintained comfortably low.

An additional equivalent thermal mass may be provided by including in the thermal distribution means 20 a portion 36 of chamber 21 located remotely from the cutting edge 3 of blade 1 (preferably, in the handle portion 10 or in the extension 11 thereof) which has a residual volume in excess of the volume of the portion of chamber 21 that is in mechanical contact with blade 1. Instead of the chamber 21 terminating at the proximal end 33, the chamber 21 may thus extend optionally to include the residual chamber 36. Similarly, the wick-like structure 22 may also extend into the residual chamber 26. This residual chamber 36, containing a relative abundance of working fluid in liquid and vapor state at the operating temperature, introduces additional thermal inertia in the system.

Figure 3:
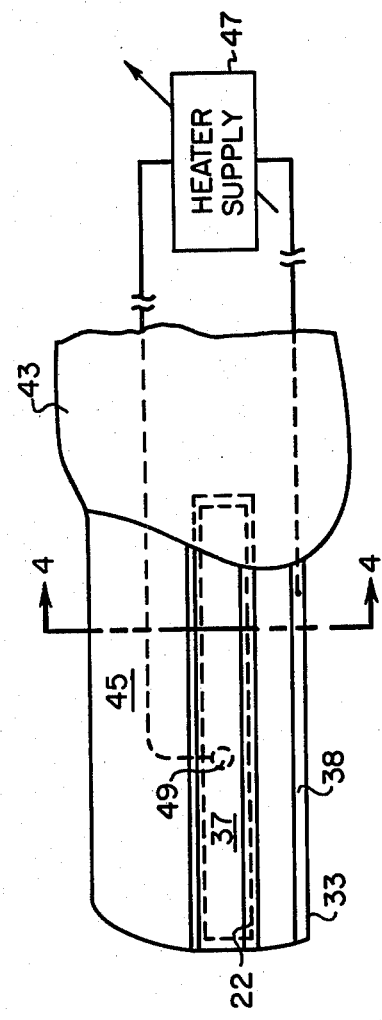
FIG. 3 is a side view of another embodiment of a hemostatic scalpel according to the present invention.
Figure 4:
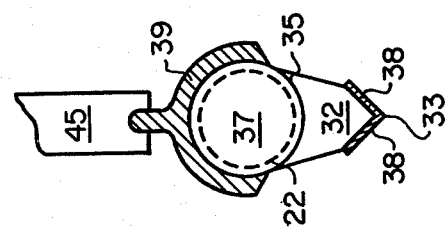
FIG. 4 is an end sectional view of the embodiment of a hemostatic scalpel according to FIG. 3.

Referring now to FIGS. 3 and 4, there is illustrated another embodiment of the present invention in which the heating means 38 is disposed contiguous the cutting edge 33 of the blade 32 which, in turn, is in good thermal contact with the lower portion of the chamber 35 of the thermal distribution means 37. Thermal insulating means 39 is positioned along the length of the cutting edge 33 of the blade 32 about the upper portion of the chamber 35. The heating means 38 is connected to receive electrical power from supply 47 which, in turn, may be controlled in response to thermal or pressure transducer 49 in a manner as previously described.

In operation, the cutting edge of the surgical instrument according to this embodiment is cooled in the regions thereof which contact tissue being cut. The heat furnished to such cooled regions by the heating means 38 located thereat is supplemented by the latent heat of vaporization which is released in such cooled regions from the vapor within the chamber 35 that condenses on the chamber walls contiguous to the cooled regions of the blade. This tends to maintain the temperature more uniform along the length of the cutting edge 33 as regions thereof are selectively cooled upon contact with tissue being cut. A resulting decrease in the average temperature or pressure within the thermal distribution means 37 is sensed by the transducer 49 to increase the applied power from source 47 to maintain the cutting edge 33 substantially isothermal during surgical manipulation thereof through tissue.

Where it is desirable to enhance the isothermal operating characteristics of the present invention, a cooling means and additional heating means may optionally be added to the embodiments of FIGS. 1–4 in mechanical and thermal coupling to the thermal distribution means. For example, cooling and heating means may be disposed about the portion of the chamber which is disposed within the handle for convenient operation. Cooling means may be provided by such conventional techniques as controlled release of a compressed gas such as nitrogen or carbon dioxide in heat-transferring relationship to the walls of the chamber. Heating means may be provided by including another electrical heater thermally coupled to the proximal end of the chamber and by operating such heater via control of the electrical power supplied thereto to maintain the thermal distribution means within the desired operating temperature range. Both the cooling means and the heating means may thus be controlled simultaneously and in thermal opposition (for example, in response to a control signal produced by a temperature or pressure transducer that is coupled to the chamber of the thermal distribution means 20 or 27) in order to provide enhanced regulation of the temperature of the cutting edge.

I claim:

1. A blade comprising:
   a cutting means including a cutting edge and thermal distribution means disposed adjacent the region of said cutting edge;
   said thermal distribution means including a fluid-tight chamber containing therein a material which has both vapor and liquid stages within a selected temperature range;
   said chamber being adapted to be heated in a selected region thereof to an elevated temperature at which said material attains the vapor state;
   said chamber providing a channel therein which is thermally coupled to said cutting edge and which transports vapor from the location of said selected region to other locations within the chamber at which conversion from the vapor to the liquid state of said material may occur;
   said chamber including therein transport means for transporting liquid back to said selected region.

2. A blade as in claim 1 wherein said transport means supports capillary action of the liquid and is disposed contiguous the inner walls of the chamber in the region of said channel.

3. A blade as in claim 1 wherein said selected region is disposed along the length of the chamber walls in the region which is opposite to the region of the chamber walls which are located adjacent the cutting edge.

4. A blade as in claim 1 wherein said selected region is disposed along the length of the chamber contiguous the portion of the walls thereof which is not adjacent to said cutting edge.

5. A blade as in claim 1 comprising heating means to heat said selected region of said chamber.

6. A blade as in claim 1 comprising insulating means disposed about the portions of the walls of the chamber except the portion adjacent the region of the cutting edge.

7. A blade as in claim 1 comprising:
   sensing means coupled to said chamber for producing a control signal which is representative of one of the pressure and temperature of the chamber; and
   means coupled to the sensing means and to said heating means for altering the power output of the heating means in response to said control signal.

8. A blade as in claim 1 wherein a portion of said chamber is located remotely from the cutting edge and includes a volume which is larger than the portion of the chamber which is adjacent the region of said cutting edge for providing thermal inertia for said cutting edge.

9. A blade as in claim 1 comprising:
   sensing means coupled to said chamber for producing a control signal which is representative of the pressure of the chamber; and
   means coupled to the sensing means and to said heating means for altering the power output of the heating means in response to said control signal.

10. A blade as in claim 1 comprising cooling means thermally coupled to said chamber for selectively altering the temperature of said cutting edge.

11. A hemostatic cutting blade comprising:
    a cutting means including a cutting edge and thermal distribution means disposed adjacent the region of said cutting edge;
    said thermal distribution means including a fluid tight chamber containing therein a material which has vapor and liquid states within a temperature range between about 300° C. to about 1000° C.;
    said chamber being adapted to be heated in a selected region thereof to an elevated temperature at which said material attains the vapor state;
    said chamber providing a channel therein which is thermally coupled to said cutting edge and which transports vapor from the location of said selected region to other locations within the chamber at which conversion from the vapor to a liquid state of said material may occur;
    said chamber including therein transport means for transporting liquid back to said selected region.

12. A hemostatic cutting blade as in claim 11 wherein said material includes one of the elements selected from the group consisting of cesium, sodium, potassium, lithium and mercury.

13. A hemostatic cutting blade comprising:
    a cutting means having a cutting edge and thermal distribution means disposed adjacent the region of said cutting edge;
    said thermal distribution means including a fluid tight chamber containing therein a material which has liquid and vapor states within a selected temperature range;
    said chamber being adapted to be heated in a selected region thereof to an elevated temperature at which said material attains the vapor state;
    said chamber providing a channel therein which is thermally coupled to said cutting edge and which transports vapor from the location of said selected region to other locations within the chamber at which conversion from the vapor to a liquid state of said material may occur;
    said chamber including therein transport means for transporting liquid back to said selected region.

14. A method of cutting using a blade having a cutting means with a cutting edge comprising the steps of heating said cutting edge from a remote heat source and selectively varying the thermal coupling between the remote heat source and regions of said cutting edge in response to cooling of regions of said cutting edge, wherein the step of selectively varying the thermal coupling, fluid is vaporized, transported and condensed within a fluid tight chamber and attains the vapor state.

15. A method of cutting as in claim 14 wherein in the step of selectively varying the thermal coupling, heated vapor is transported from the heat source to locations adjacent regions of the cutting edge where the vapor is condensed to liquid for return to the heat source for heating and vaporization.

16. A method of cutting using a blade having a cutting means with a cutting edge comprising the steps of:
    heating said cutting edge from a remote heat source and selectively varying the thermal coupling between the remote heat source and regions of said cutting edge in response to cooling of regions of said cutting edge, wherein the step of selectively varying the thermal coupling, fluid is vaporized, transported and condensed within a fluid-tight chamber;

comprising the additional step of sensing at least one of the pressure and temperature within the chamber to control the heat source.

17. A method of cutting as in claim 16 wherein in the step of vaporizing fluid, heat from a heat source is applied to the chamber at at least one of the locations near one end of the chamber, and the location along the chamber in regions thereabout which are substantially opposite the cutting edge.

* * * * *